US011857375B2

(12) United States Patent
Koshino et al.

(10) Patent No.: US 11,857,375 B2
(45) Date of Patent: Jan. 2, 2024

(54) MEDICAL IMAGING SYSTEM

(71) Applicant: FUJIFILM Corporation, Tokyo (JP)

(72) Inventors: Riko Koshino, Tokyo (JP); Shun Hotta, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 152 days.

(21) Appl. No.: 16/852,552

(22) Filed: Apr. 20, 2020

(65) Prior Publication Data

US 2020/0397410 A1 Dec. 24, 2020

(30) Foreign Application Priority Data

Jun. 21, 2019 (JP) ................. 2019-115669

(51) Int. Cl.
*A61B 8/08* (2006.01)
*A61B 8/00* (2006.01)

(52) U.S. Cl.
CPC .......... *A61B 8/5261* (2013.01); *A61B 8/0825* (2013.01); *A61B 8/403* (2013.01); *A61B 8/4416* (2013.01); *A61B 8/469* (2013.01); *A61B 8/54* (2013.01)

(58) Field of Classification Search
CPC ..... A61B 8/5261; A61B 8/0825; A61B 8/403; A61B 8/4416; A61B 6/0414; A61B 8/469; A61B 8/54; A61B 6/4417; A61B 6/502; A61B 6/5247
See application file for complete search history.

(56) References Cited

U.S. PATENT DOCUMENTS

| | | | |
|---|---|---|---|
| 9,788,806 | B2 | 10/2017 | Hamauzu |
| 9,901,320 | B2 | 2/2018 | DeFreitas et al. |
| 10,226,224 | B2 | 3/2019 | Arai et al. |
| 10,390,785 | B2 | 8/2019 | Arai et al. |
| 10,448,917 | B2 | 10/2019 | Arai et al. |
| 11,129,594 | B2 | 9/2021 | Sendai |
| 2011/0230759 | A1 | 9/2011 | Muller |

(Continued)

FOREIGN PATENT DOCUMENTS

| | | |
|---|---|---|
| JP | 2011200655 | 10/2011 |
| JP | 2013545545 | 12/2013 |

(Continued)

OTHER PUBLICATIONS

"Office Action of Japan Counterpart Application", dated Jul. 5, 2022, with English translation thereof, p. 1-p. 7.

*Primary Examiner* — Peter Luong
(74) *Attorney, Agent, or Firm* — JCIPRNET

(57) ABSTRACT

A medical imaging system acquires a first medical image of a breast as an object using a first imaging apparatus in a state in which the breast is fixed, captures a second medical image of the breast as the object using a second imaging apparatus having a different imaging principle from the first imaging apparatus in a state in which the fixation of the breast is maintained, sets a period for which the second medical image is captured and a period for which the first medical image is analyzed so as to at least partially overlap each other in a case in which the first medical image is analyzed to detect a region of interest, and outputs positional information such that a region-of-interest image having the region of interest as a main object is captured in a case in which the region of interest has been detected.

20 Claims, 12 Drawing Sheets

(56) References Cited

U.S. PATENT DOCUMENTS

| | | | | |
|---|---|---|---|---|
| 2012/0035462 | A1* | 2/2012 | Maurer, Jr. | A61B 90/39 |
| | | | | 600/431 |
| 2013/0237814 | A1* | 9/2013 | Marcovici | A61B 6/025 |
| | | | | 600/427 |
| 2013/0281840 | A1* | 10/2013 | Vaughan | A61B 6/4078 |
| | | | | 600/425 |
| 2014/0135623 | A1* | 5/2014 | Manak | A61B 8/5261 |
| | | | | 600/427 |
| 2014/0180082 | A1* | 6/2014 | Evans | A61B 8/0825 |
| | | | | 600/427 |
| 2015/0305700 | A1* | 10/2015 | Wendler | A61B 8/4263 |
| | | | | 600/424 |
| 2016/0007947 | A1* | 1/2016 | Spencer | G01S 15/8952 |
| | | | | 600/424 |
| 2016/0166234 | A1* | 6/2016 | Zhang | A61B 8/403 |
| | | | | 600/427 |
| 2017/0360389 | A1* | 12/2017 | Ochiai | A61B 6/502 |
| 2018/0249985 | A1 | 9/2018 | DeFreitas et al. | |

FOREIGN PATENT DOCUMENTS

| | | |
|---|---|---|
| JP | 2014504918 | 2/2014 |
| JP | 2016190012 | 11/2016 |
| JP | 2017153571 | 9/2017 |
| JP | 2017176509 | 10/2017 |
| JP | 2017225484 | 12/2017 |
| JP | 2017225635 | 12/2017 |
| WO | 2019091807 | 5/2019 |

* cited by examiner

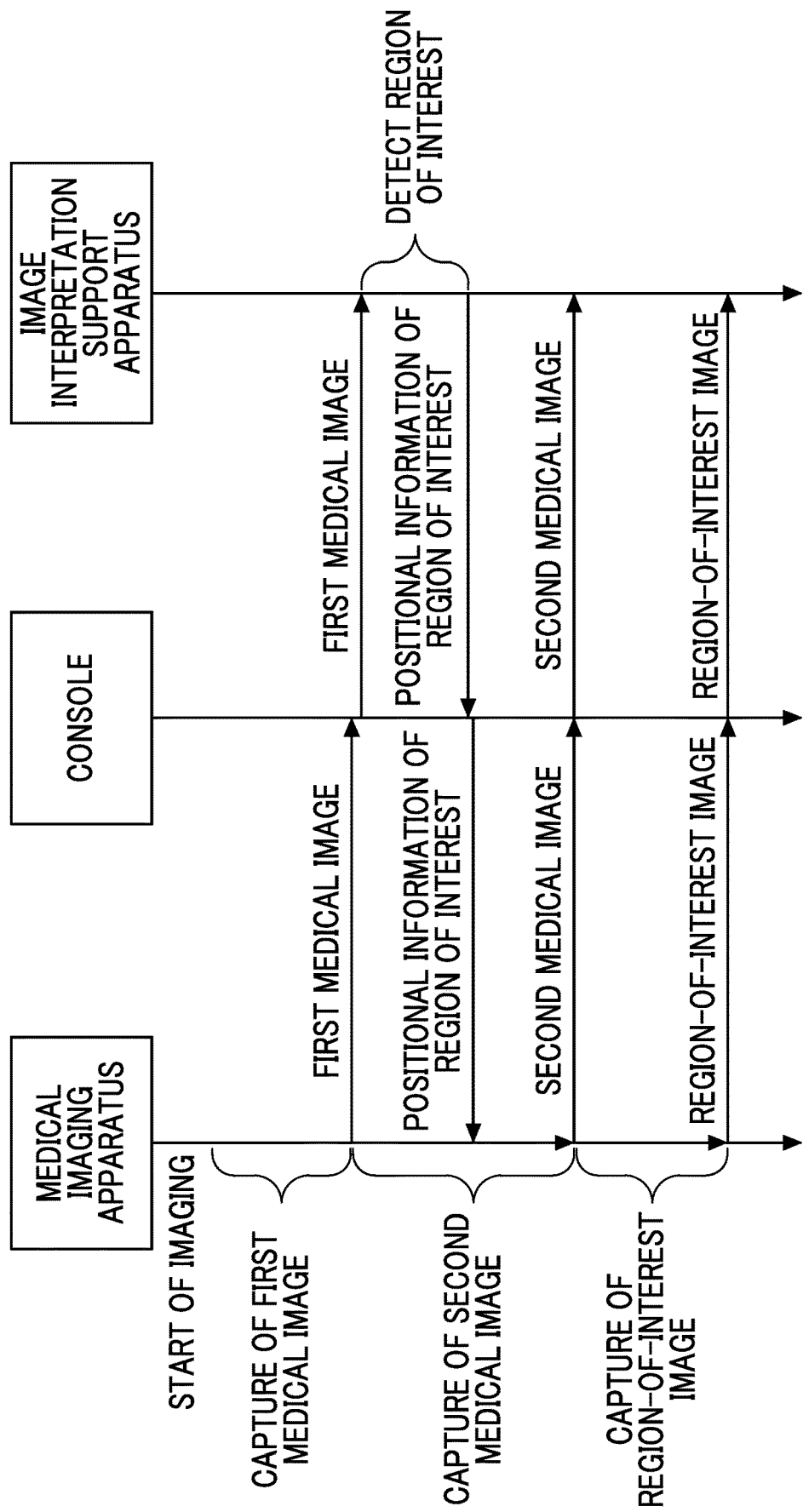

MEDICAL IMAGING SYSTEM

CROSS-REFERENCE TO RELATED APPLICATIONS

The present application claims priority under 35 U.S.C. § 119 to Japanese Patent Application No. 2019-115669 filed on Jun. 21, 2019, Each of the above application is hereby expressly incorporated by reference, in its entirety, into the present application.

BACKGROUND OF THE INVENTION

1. Field of the Invention

The present disclosure relates to a medical imaging system.

2. Description of the Related Art

JP2014-504918A discloses a medical imaging system that irradiates the breast as an object with radiation to acquire a radiographic image and detects a region of interest from the acquired radiographic image. The medical imaging system captures an ultrasound image of the region of interest detected using the radiographic image.

SUMMARY OF THE INVENTION

The medical imaging system described in JP2014-504918A captures a first medical image (for example, a radiographic image) of the breast as an object and a second medical image (for example, an ultrasound image) obtained by a different imaging principle from the first medical image. However, in some cases, it is difficult to know which of the first medical image and the second medical image is useful for diagnosis before imaging, depending on, for example, the patient and the type of lesion. It is preferable to obtain a region-of-interest image, which is a medical image having a region of interest as a main object, for the region of interest, such as a lesion, in order for a user, such as a radiologist, to make an effective diagnosis.

However, for example, in a case in which the first medical image is analyzed to detect the region of interest and the region-of-interest image is captured on the basis of the detected region of interest after both the first medical image and the second medical image are obtained, the user does not always immediately interpret the image. In this case, the patient waits at the hospital until the interpretation of the image by the user is completed, or returns home once and has to visit the hospital again on another day. As a result, a burden on the patient increases.

The present disclosure has been made in view of the above-mentioned problems and an object of the present disclosure is to provide a medical imaging system that can reduce a burden on a patient.

According to the present disclosure, there is provided a medical imaging system comprising: an acquisition unit that acquires a first medical image obtained by capturing an image of a breast as an object using a first imaging apparatus in a state in which the breast is fixed; an imaging control unit that performs control to capture a second medical image of the breast as the object using a second imaging apparatus having a different imaging principle from the first imaging apparatus in a state in which the fixation of the breast is maintained, after the first medical image is captured; an analysis unit that analyzes the first medical image to detect a region of interest for a period that at least partially overlaps a period for which the second medical image is captured; and an output unit that, in a case in which the analysis unit detects the region of interest, outputs positional information indicating a position of the region of interest such that a region-of-interest image having the region of interest as a main object is captured by the same imaging principle as that of the first imaging apparatus under different imaging conditions from the first medical image or is captured by the same imaging principle as that of the second imaging apparatus under different imaging conditions from the second medical image, further the second medical image is captured by the second imaging apparatus.

In the medical imaging system according to the present disclosure, the imaging control unit may perform control to capture the second medical image in a state in which a force of fixing the breast is different from that in the capture of the first medical image.

In the medical imaging system according to the present disclosure, the first medical image may be obtained by irradiating the breast with radiation and the second medical image may be obtained by irradiating the breast with ultrasonic waves.

In the medical imaging system according to the present disclosure, the imaging control unit may perform control to capture the region-of-interest image on the basis of the positional information.

The medical imaging system according to the present disclosure may further comprise: a compression member that compresses and fixes the breast; and a compression control unit that performs control to set a compression force of the compression member against the breast as a first force in the capture of the first medical image and to set the compression force of the compression member against the breast as a second force less than the first force in the capture of the second medical image.

In the medical imaging system according to the present disclosure, the second force may be a force at which an amount of change in a thickness of the breast in a case in which the compressed state is changed from a state in which the breast is compressed with the first force to a state in which the breast is compressed with the second force is equal to or less than a predetermined amount of change.

In the medical imaging system according to the present disclosure, the imaging control unit may perform control to capture the region-of-interest image while generating the ultrasonic waves to the region of interest at a plurality of different angles in a state in which the breast is compressed with the same compression force as the compression force against the breast in the capture of the second medical image.

In the medical imaging system according to the present disclosure, the imaging control unit may perform control to capture the region-of-interest image while changing the compressed state of the breast.

In the medical imaging system according to the present disclosure, the compression control unit may perform control to release the compressed state of the breast in a case in which the analysis unit does not detect the region of interest.

According to the present disclosure, it is possible to reduce a burden on a patient.

BRIEF DESCRIPTION OF THE DRAWINGS

FIG. 14 is a sequence diagram illustrating an example of the overall flow of the imaging process.

DESCRIPTION OF THE PREFERRED EMBODIMENTS

Hereinafter, an embodiment according to the technology of the present disclosure will be described in detail with reference to the drawings.

Figure 1:
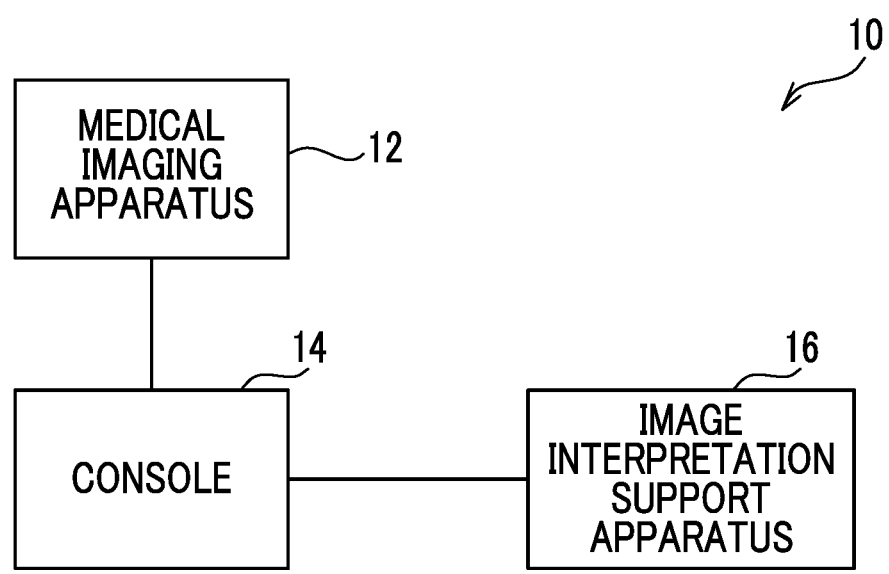
FIG. 1 is a block diagram illustrating an example of the configuration of a medical imaging system.

First, the configuration of a medical imaging system 10 according to this embodiment will be described with reference to FIG. 1. As illustrated in FIG. 1, the medical imaging system 10 comprises a medical imaging apparatus 12, a console 14, and an image interpretation support apparatus 16. The medical imaging apparatus 12 and the console 14 are connected so as to be able to communicate with each other, and the console 14 and the image interpretation support apparatus 16 are connected so as to be able to communicate with each other. The medical imaging apparatus 12 and the console 14 are operated by a radiographer, such as a radiology technician, and the image interpretation support apparatus 16 is operated by an image interpreter, such as a doctor.

Next, the configuration of the medical imaging apparatus 12 according to this embodiment will be described with reference to FIGS. 2 to 4. The medical imaging apparatus 12 has the functions of a mammography apparatus that irradiates the breast of a subject as an object with radiation R (for example, X-rays) to capture a radiographic image of the breast, and the functions of an ultrasonography apparatus that transmits ultrasonic waves to the breast, receives ultrasonic echoes reflected in the breast, and captures an ultrasound image. That is, the medical imaging apparatus 12 can capture two types of medical images having different imaging principles, that is, a radiographic image and an ultrasound image. The medical imaging apparatus 12 may be an apparatus that captures the image of the breast of the subject not only in a state in which the subject stands up (standing state) but also in a state in which the subject sits on, for example, a chair (including a wheelchair) (sitting state).

Figure 2:
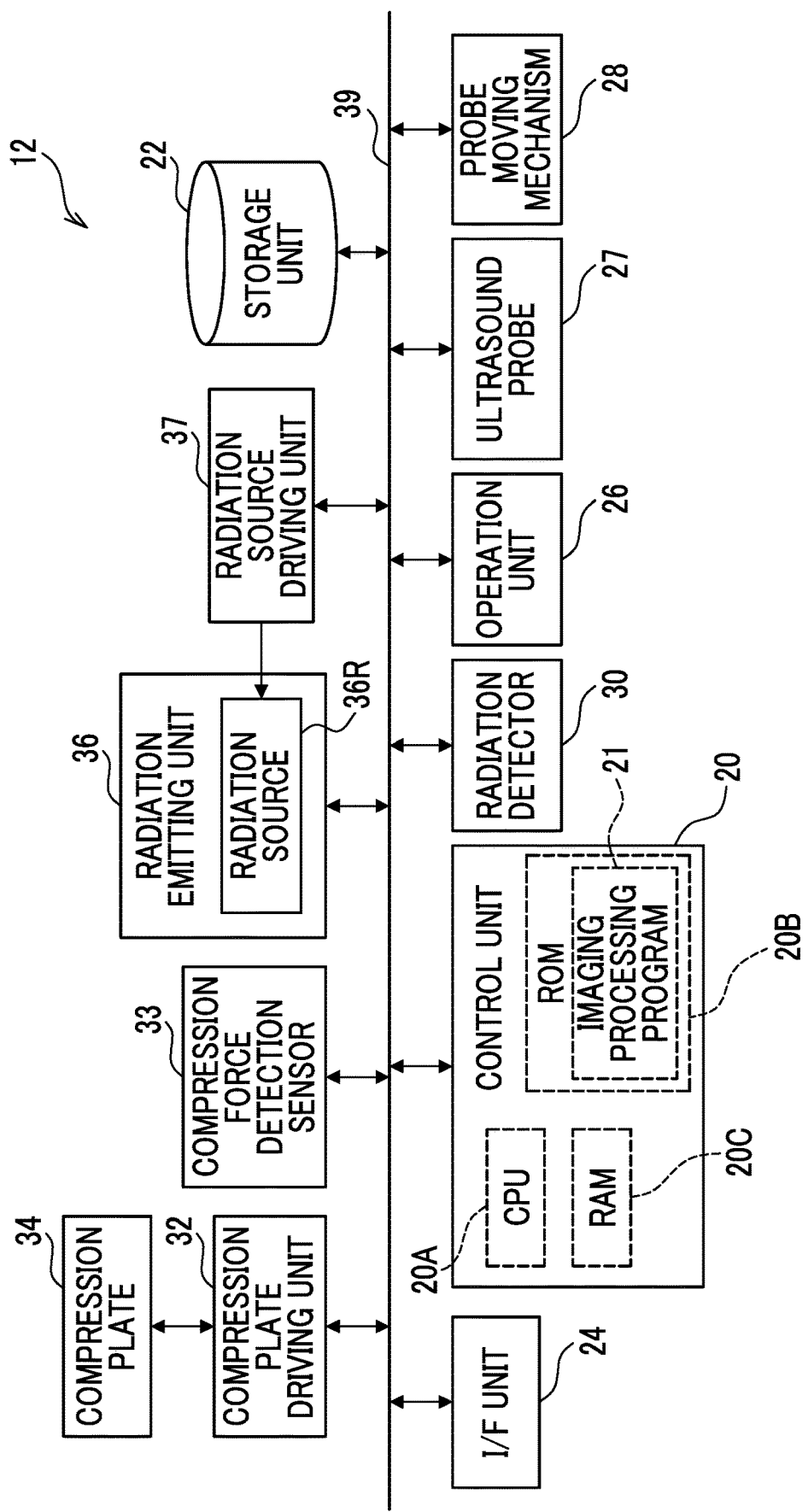
FIG. 2 is a block diagram illustrating an example of the hardware configuration of a medical imaging apparatus.

As illustrated in FIG. 2, the medical imaging apparatus 12 comprises a control unit 20, a storage unit 22, an interface (I/F) unit 24, an operation unit 26, an ultrasound probe 27, and a probe moving mechanism 28. Further, the medical imaging apparatus 12 comprises a radiation detector 30, a compression plate driving unit 32, a compression force detection sensor 33, a compression plate 34, a radiation emitting unit 36, and a radiation source driving unit 37. The control unit 20, the storage unit 22, the I/F unit 24, the operation unit 26, the ultrasound probe 27, and the probe moving mechanism 28 are connected to each other through a bus 39 such that they can transmit and receive various kinds of information. Further, the radiation detector 30, the compression plate driving unit 32, the compression force detection sensor 33, the radiation emitting unit 36, and the radiation source driving unit 37 are connected to each other through the bus 39 such that they can transmit and receive various kinds of information.

The control unit 20 controls the overall operation of the medical imaging apparatus 12 under the control of the console 14. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a medical image are stored in the ROM 20B in advance. The RAM 20C temporarily stores various kinds of data.

The radiation detector 30 detects the radiation R transmitted through the breast which is an object. As illustrated in FIG. 3, the radiation detector 30 is provided in an imaging table 40. In the medical imaging apparatus 12 according to this embodiment, in a case in which imaging is performed, the breast of the subject is positioned on an imaging surface 40A of the imaging table 40 by a radiographer. For example, the imaging surface 40A with which the breast of the subject comes into contact is made of carbon in terms of the transmission and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

For example, the image data indicating the radiographic image captured by the radiation detector 30 and various other kinds of information are stored in the storage unit 22. Examples of the storage unit 22 include a hard disk drive (HDD) and a solid state drive (SSD). The I/F unit 24 transmits and receives various kinds of information to and from the console 14 using wireless communication or wired communication. The image data indicating the radiographic image captured by the radiation detector 30 in the medical imaging apparatus 12 is transmitted to the console 14 through the I/F unit 24.

The operation unit 26 is provided as a plurality of switches in, for example, the imaging table 40 of the medical imaging apparatus 12. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a compression unit 46. The medical imaging apparatus 12 according to this embodiment comprises the arm portion 42, a base 44, and a shaft portion 45. The arm portion 42 is supported by the base 44 so as to be movable in the up-down direction (Z-axis direction). The shaft portion 45 connects the arm portion 42 to the base 44. The radiation source driving unit 37 can relatively rotate the arm portion 42 with respect to the base 44, using the shaft portion 45 as a rotation axis.

Figure 3:
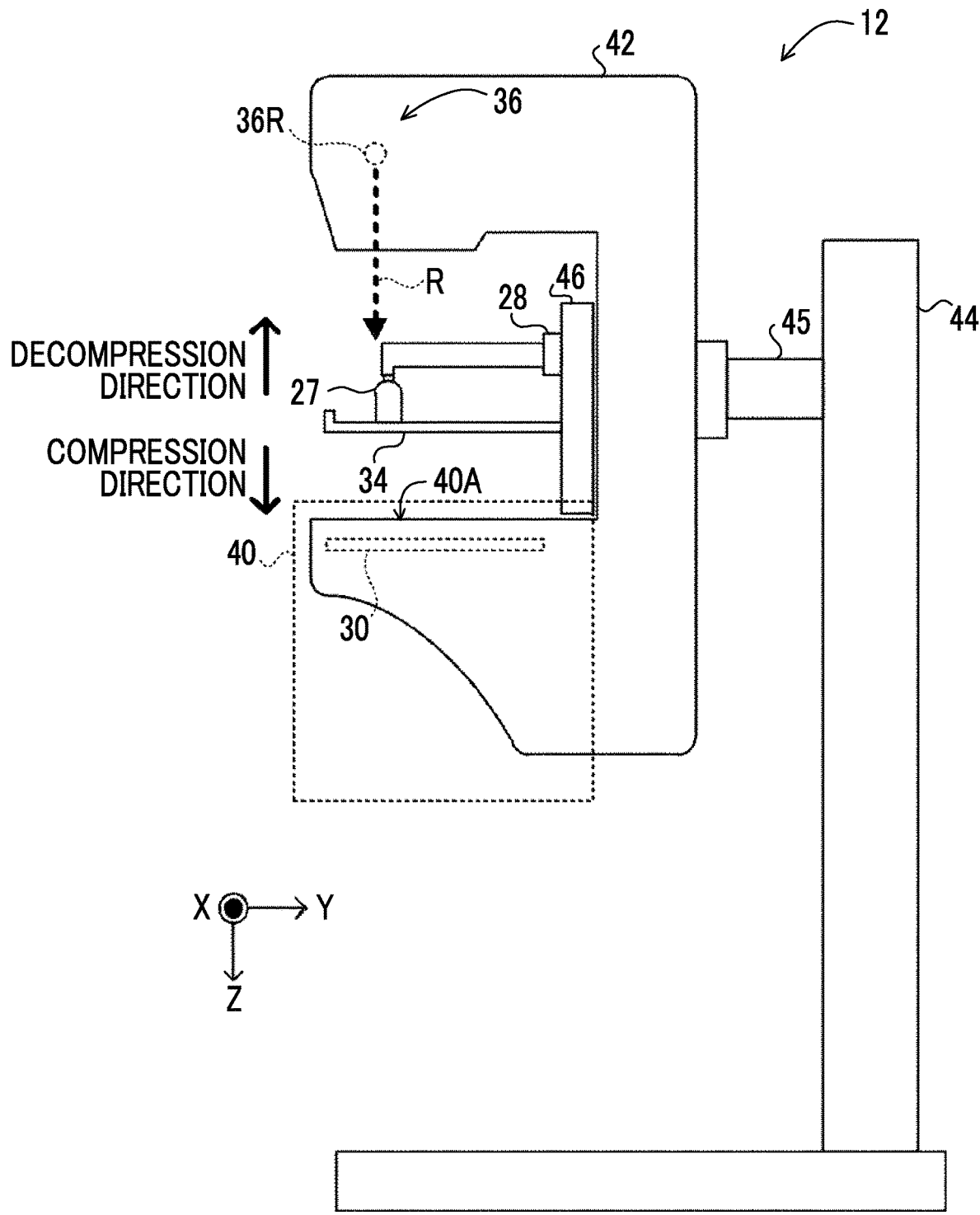
FIG. 3 is a side view illustrating an example of the outward appearance of the medical imaging apparatus.
Figure 4:
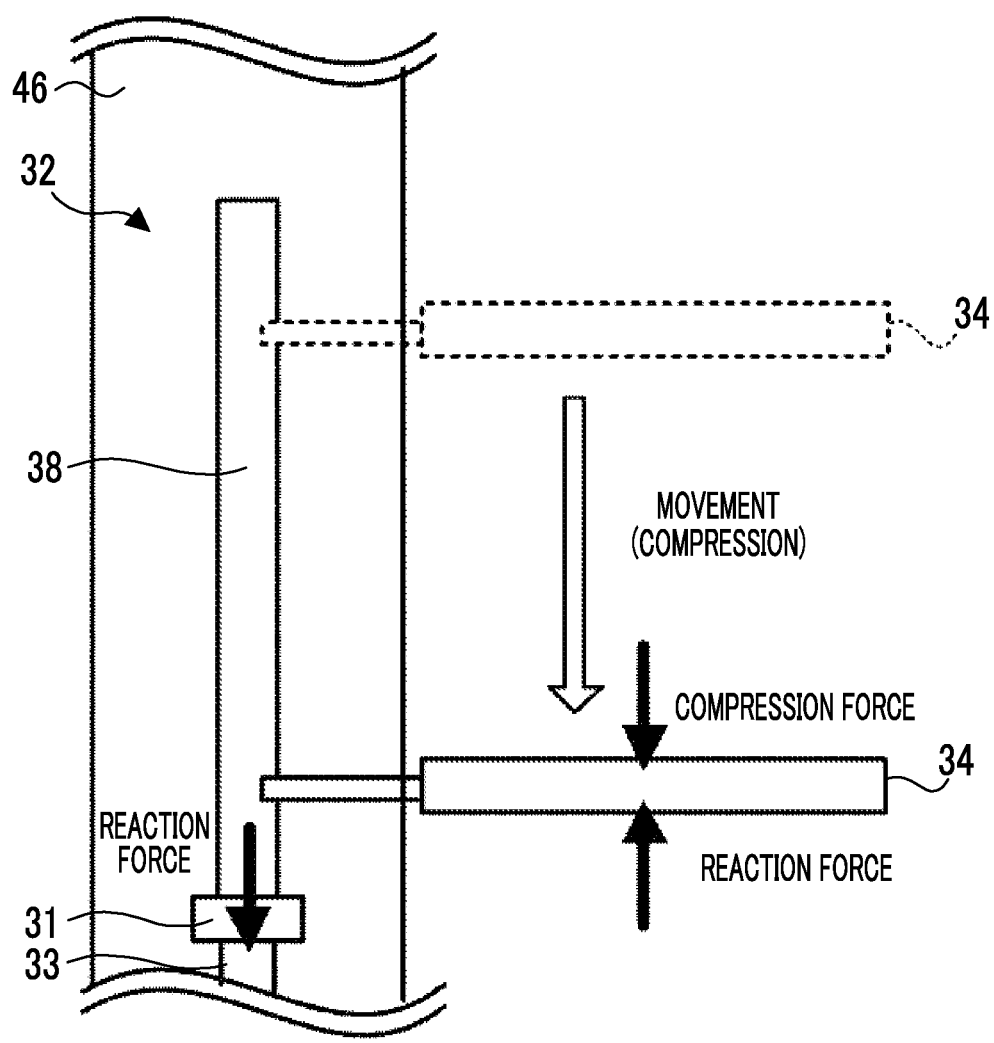
FIG. 4 is a diagram illustrating an example of a configuration in a case in which a compression force is detected by a load applied to a motor.

As illustrated in FIGS. 3 and 4, the compression plate driving unit 32, the compression force detection sensor 33, and the compression plate 34 are provided in the compression unit 46. The compression unit 46 and the arm portion 42 can be relatively rotated with respect to the base 44 separately, using the shaft portion 45 as a rotation axis. In this embodiment, gears (not illustrated) are provided in each of the shaft portion 45, the arm portion 42, and the compression unit 46. Each gear is switched between an engaged state and a disengaged state to connect each of the arm portion 42 and the compression unit 46 to the shaft portion 45. One or both of the arm portion 42 and the compression unit 46 connected to the shaft portion 45 are rotated integrally with the shaft portion 45.

The compression plate 34 according to this embodiment is a plate-shaped compression member that compresses and fixes the breast and is moved in the up-down direction (Z-axis direction) by the compression plate driving unit 32 to compress the breast of the subject against the imaging table 40. Hereinafter, for the movement direction of the compression plate 34, the direction in which the breast is compressed, that is, the direction in which the compression plate 34 becomes closer to the imaging surface 40A is referred to as a "compression direction" and the direction in which the compression of the breast is released, that is, the direction in which the compression plate 34 becomes closer to the radiation emitting unit 36 is referred to as a "decompression direction". It is preferable that the compression plate 34 is transparent in order to check positioning or a compressed state in the compression of the breast. In addition, the compression plate 34 is made of a material having high transmittance for the radiation R.

As illustrated in FIG. 4, the compression unit 46 comprises the compression plate driving unit 32 including a motor 31 and a ball screw 38 and the compression force detection sensor 33. The compression force detection sensor 33 detects the compression force of the compression plate 34 against the entire breast. In the example illustrated in FIG. 4, the compression force detection sensor 33 detects the compression force on the basis of load applied to the motor 31 as a driving source of the compression plate 34. The compression plate 34 is supported by the ball screw 38 and the motor 31 is driven to slide the compression plate 34 between the imaging table 40 and the radiation source 36R. The compression force detection sensor 33 according to this embodiment is a strain gauge, such as a load cell. The compression force detection sensor 33 detects reaction force to the compression force of the compression plate 34 to detect the compression force of the compression plate 34 against the breast.

A method for detecting the compression force is not limited to the configuration illustrated in FIG. 4. For example, the compression force detection sensor 33 may be a semiconductor pressure sensor or a capacitive pressure sensor. Further, for example, the compression force detection sensor 33 may be provided in the compression plate 34.

As illustrated in FIG. 3, the ultrasound probe 27 and the probe moving mechanism 28 are provided in the compression unit 46. The ultrasound probe 27 is moved along an upper surface (a surface opposite to the surface on which the breast of the subject is placed) of the compression plate 34 by the probe moving mechanism 28 and scans the breast with ultrasonic waves to acquire an ultrasound image of the breast. The ultrasound probe 27 comprises a plurality of ultrasound transducers (not illustrated) that are arranged one-dimensionally or two-dimensionally. Each of the ultrasound transducers included in the ultrasound probe 27 transmits ultrasonic waves on the basis of a driving signal applied, receives ultrasonic echoes, and outputs a received signal.

Each of the ultrasound transducers included in the ultrasound probe 27 is, for example, a transducer in which electrodes are formed at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave driving signal is transmitted to apply a voltage to the electrodes of the transducer, the piezoelectric body is expanded and contracted. Pulsed or continuous ultrasonic waves are generated from each transducer by the expansion and contraction and the generated ultrasonic waves are combined to form an ultrasound beam. In addition, each transducer receives the propagated ultrasonic waves and is then expanded and contracted to generate an electric signal. The generated electric signal is output as a received ultrasound signal and is input to the console 14.

In a case in which ultrasonography is performed, the ultrasound probe 27 is moved along the upper surface of the compression plate 34 in a state in which an acoustic matching member, such as echo jelly, is applied onto the upper surface of the compression plate 34. In the medical imaging apparatus 12 according to this embodiment, the control unit 20 can direct the probe moving mechanism 28 to move the ultrasound probe 27, thereby automatically capturing an ultrasound image.

Figure 5:
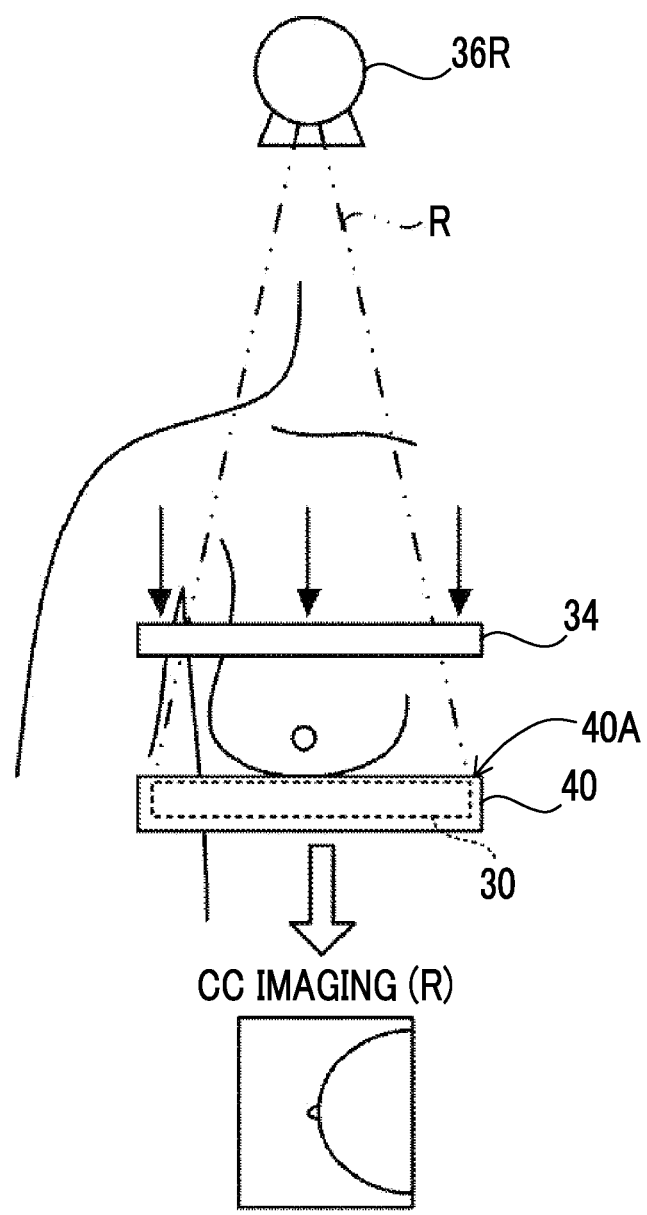
FIG. 5 is a diagram illustrating an aspect of CC imaging.
Figure 6:
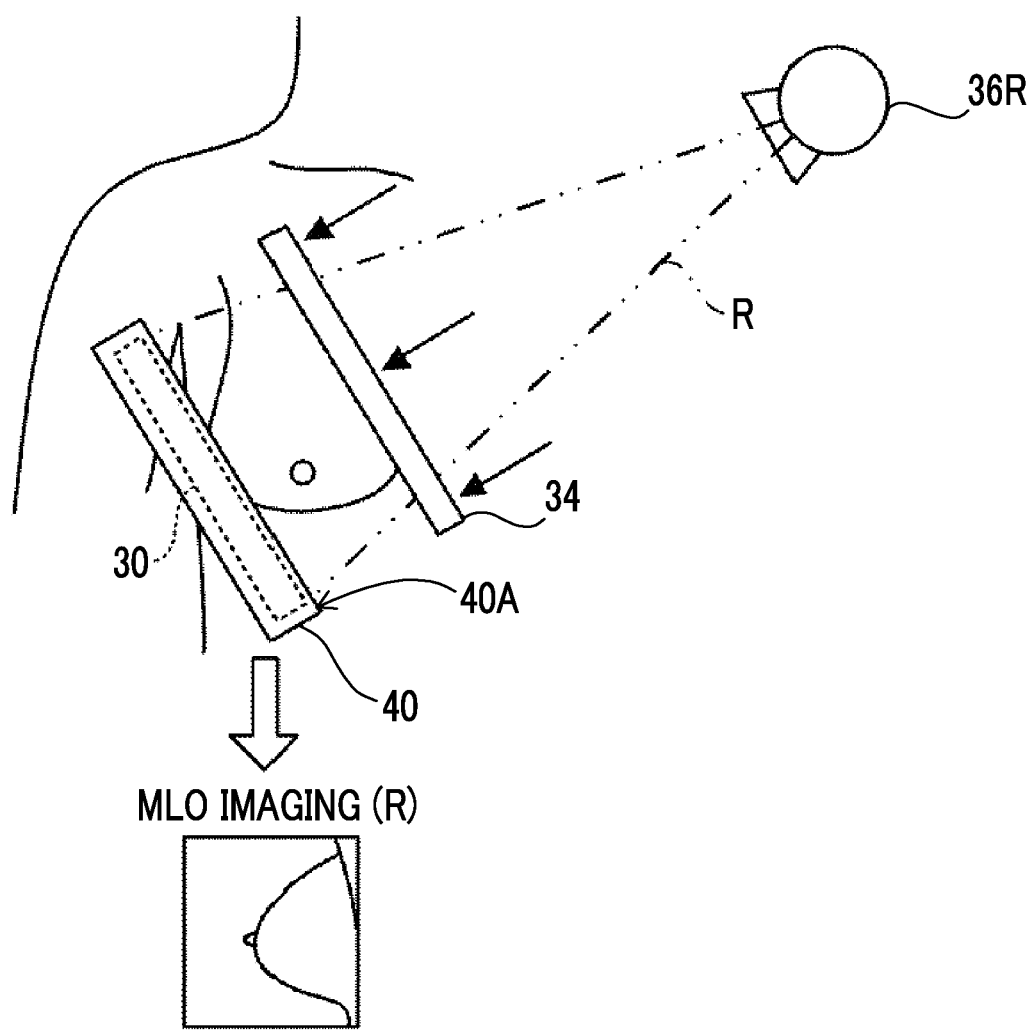
FIG. 6 is a diagram illustrating an aspect of MLO imaging.

FIG. 5 illustrates an aspect of cranio-caudal (CC) imaging that is simple imaging in which the radiation source 36R is disposed on a normal line passing through the center of the detection surface of the radiation detector 30 so as to face the detection surface and emits the radiation R, the breast is vertically sandwiched and compressed, and an image of the breast is captured. In contrast, FIG. 6 illustrates an aspect of medio-lateral oblique (MLO) imaging which is simple imaging and in which the breast is obliquely sandwiched and compressed and an image of the breast is captured. FIGS. 5 and 6 illustrate examples in which the right breast is the object. However, the CC imaging and the MLO imaging are similarly performed for the left breast.

In a case in which a radiographic image is captured, the control unit 20 according to this embodiment controls the radiation emitting unit 36, the radiation detector 30, and the compression plate driving unit 32. The control unit 20 directs the compression plate driving unit 32 to move the compression plate 34 on the basis of the detection result of the compression force detection sensor 33, thereby compressing the breast against the imaging table 40. The control unit 20 adjusts imaging conditions, such as a tube voltage and a tube current, and directs the radiation source 36R of the radiation emitting unit 36 to emit the radiation R. The control unit 20 directs the radiation detector 30 to detect the radiation R transmitted through the breast, thereby capturing a radiographic image.

Further, in a case in which an ultrasound image is captured, the control unit 20 controls the ultrasound probe 27 and the probe moving mechanism 28 in a state in which the breast is compressed by the compression plate 34. The control unit 20 checks the position of the ultrasound probe 27 on the basis of the detection result of a sensor (not illustrated) that detects the position of the ultrasound probe 27 and directs the probe moving mechanism 28 to move the ultrasound probe 27. The control unit 20 directs the ultrasound probe 27 to transmit and receive ultrasonic waves while moving the ultrasound probe 27 using the probe moving mechanism 28, thereby capturing an ultrasound image.

The portion (for example, the radiation emitting unit 36 and the radiation detector 30) controlled by the control unit 20 in a case in which a radiographic image is captured is an example of a first imaging apparatus according to the technology of the present disclosure. In addition, the portion (for example, the ultrasound probe 27 and the probe moving mechanism 28) controlled by the control unit 20 in a case in which an ultrasound image is captured is an example of a second imaging apparatus according to the technology of the present disclosure.

Figure 7:
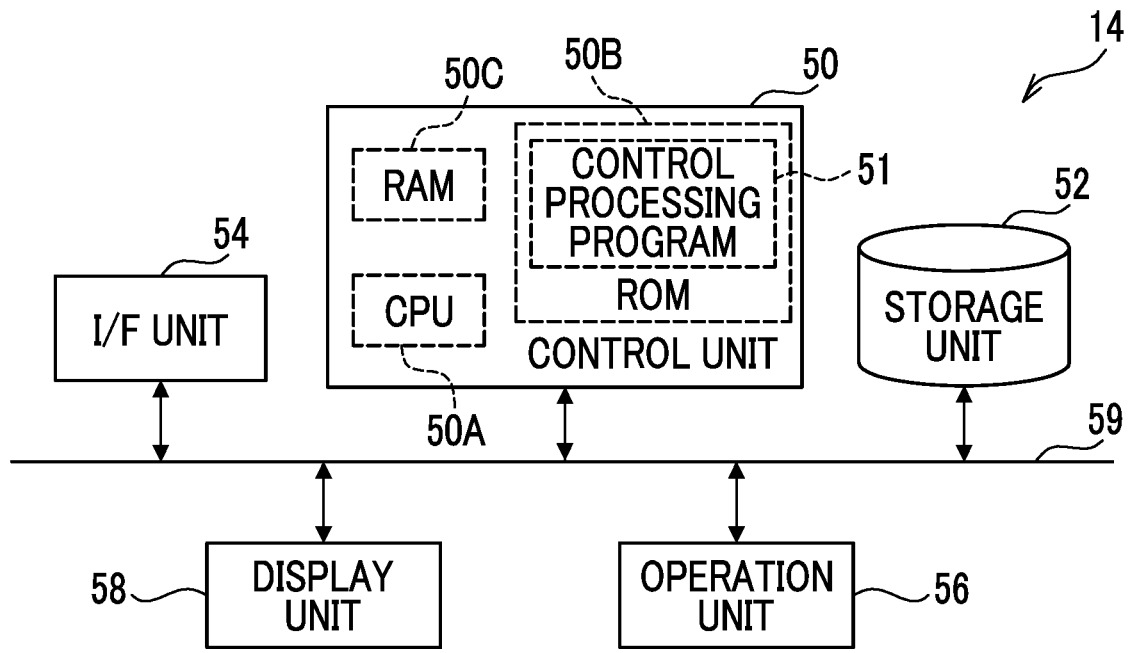
FIG. 7 is a block diagram illustrating an example of the hardware configuration of a console.

Next, the hardware configuration of the console 14 according to this embodiment will be described with reference to FIG. 7. The console 14 inputs an imaging order and various kinds of information acquired from, for example, a radiology information system (RIS) through a network and commands input by the user through, for example, an operation unit 56 to the medical imaging apparatus 12. As illustrated in FIG. 7, the console 14 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59 such that they can transmit and receive various kinds of information. Examples of the console 14 include information processing apparatuses such as a personal computer and a server computer.

The control unit 50 controls the overall operation of the console 14. The control unit 50 comprises a CPU 50A, a ROM 50B, and a RAM 50C. Various programs including a control processing program 51 executed by the CPU 50A are stored in the ROM 50B in advance. The RAM 50C temporarily stores various kinds of data. The storage unit 52 stores, for example, image data indicating the medical image captured by the medical imaging apparatus 12 and various other kinds of information. Examples of the storage unit 52 include an HDD and an SSD.

The operation unit 56 is used by the user to input, for example, commands related to the capture of a medical image and various kinds of information. Therefore, the operation unit 56 according to this embodiment includes an irradiation command button that is pressed by the user to command the emission of the radiation R. The operation unit 56 is not particularly limited. Examples of the operation unit 56 include various switches, a touch panel, a touch pen, and a mouse. The display unit 58 displays various kinds of information. The operation unit 56 and the display unit 58 may be integrated into a touch panel display. The I/F unit 54 transmits and receives various kinds of information to and from the medical imaging apparatus 12 and the image interpretation support apparatus 16 using wireless communication or wired communication.

Figure 8:
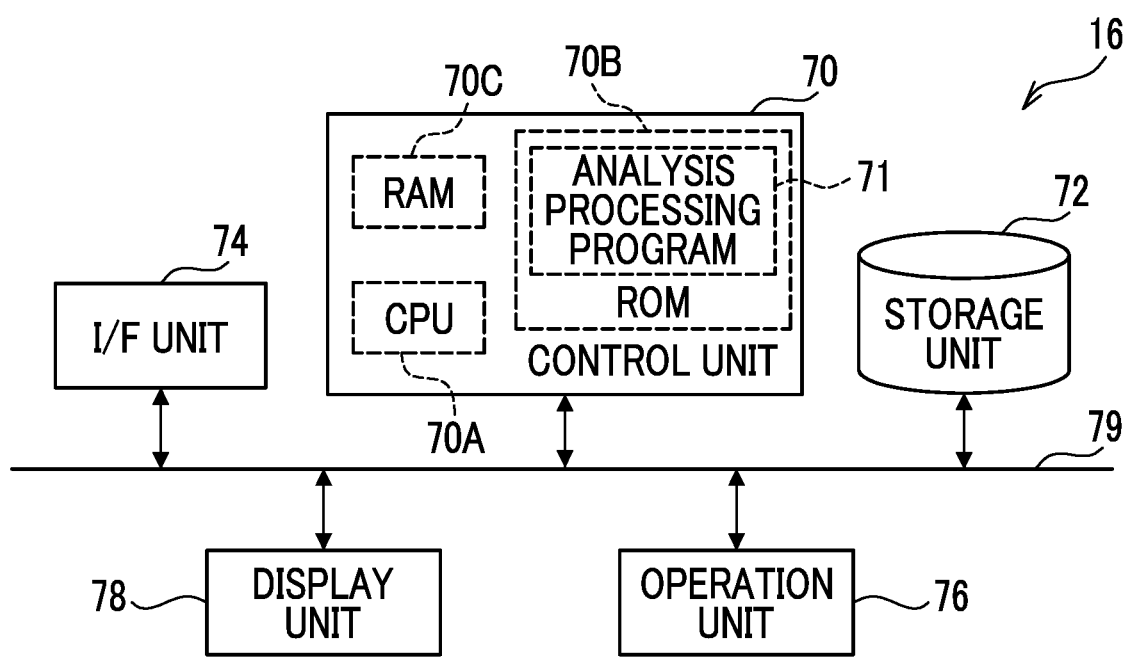
FIG. 8 is a block diagram illustrating an example of the hardware configuration of an image interpretation support apparatus.

Next, the hardware configuration of the image interpretation support apparatus 16 according to this embodiment will be described with reference to FIG. 8. As illustrated in FIG. 8, the image interpretation support apparatus 16 comprises a control unit 70, a storage unit 72, an I/F unit 74, an operation unit 76, and a display unit 78. The control unit 70, the storage unit 72, the I/F unit 74, the operation unit 76, and the display unit 78 are connected to each other through a bus 79 such that they can transmit and receive various kinds of information. Examples of the image interpretation support apparatus 16 include information processing apparatuses such as a personal computer and a server computer.

The control unit 70 controls the overall operation of the image interpretation support apparatus 16. The control unit 70 includes a CPU 70A, a ROM 70B, and a RAM 70C. Various programs including an analysis processing program 71 executed by the CPU 70A are stored in the ROM 70B in advance. The RAM 70C temporarily stores various kinds of data. The storage unit 72 stores image data indicating the medical image transmitted from the console 14 and other various kinds of information. Examples of the storage unit 72 include an HDD and an SSD.

The operation unit 76 includes, for example, a mouse and a keyboard and is used for the operation of the user. The display unit 78 displays various kinds of information. The operation unit 76 and the display unit 78 may be integrated into a touch panel display. The I/F unit 74 transmits and receives various kinds of information to and from the console 14 using wireless communication or wired communication.

Figure 9:
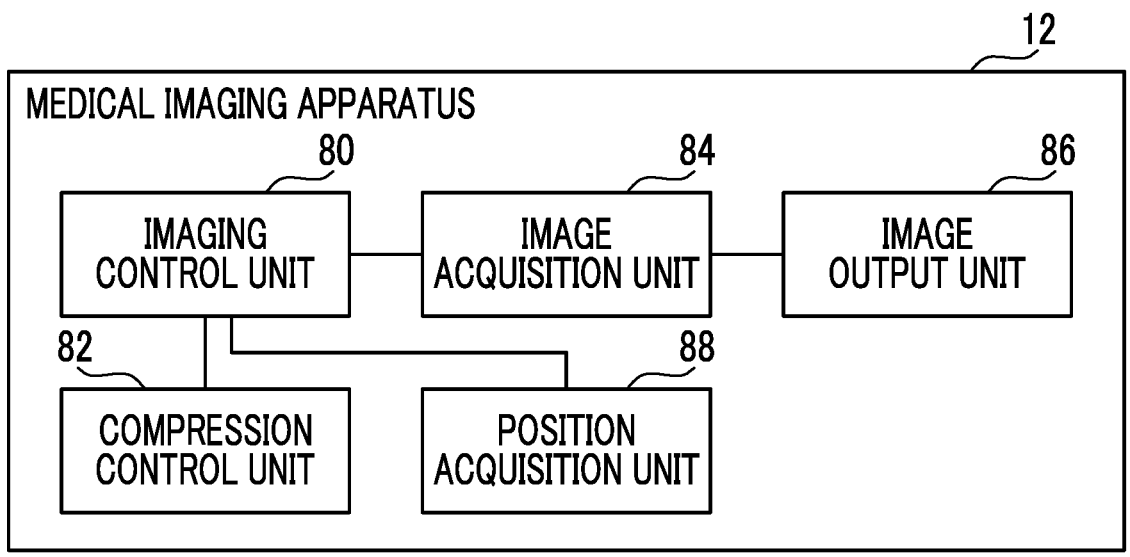
FIG. 9 is a block diagram illustrating an example of the functional configuration of the medical imaging apparatus.

Next, the functional configuration of the medical imaging apparatus 12 according to this embodiment will be described with reference to FIG. 9. As illustrated in FIG. 9, the medical imaging apparatus 12 comprises an imaging control unit 80, a compression control unit 82, an image acquisition unit 84, an image output unit 86, and a position acquisition unit 88. The CPU 20A executes the imaging processing program 21 to function as the imaging control unit 80, the compression control unit 82, the image acquisition unit 84, the image output unit 86, and the position acquisition unit 88.

The imaging control unit 80 controls the radiation emitting unit 36 and the radiation detector 30 such that a radiographic image is captured in a state in which the breast as an object is fixed by the compression plate 34. Hereinafter, the radiographic image captured by this control is referred to as a "first medical image".

In addition, the imaging control unit 80 controls the ultrasound probe 27 and the probe moving mechanism 28 such that an ultrasound image is captured in a state in which the fixation of the breast as an object is maintained after the first medical image is captured. Hereinafter, the ultrasound image captured by this control is referred to as a "second medical image". In addition, the state in which the fixation of the breast is maintained includes a case in which the breast is fixed with the same fixing force and a case in which the fixing force is changed without releasing the fixation of the breast. In this embodiment, the imaging control unit 80 performs control to capture the second medical image in a state in which the force of fixing the breast is different from that in a case in which the first medical image is captured.

Further, after the second medical image is captured, the imaging control unit 80 controls the ultrasound probe 27 and the probe moving mechanism 28 on the basis of positional information indicating the position of a region of interest acquired by the position acquisition unit 88 which will be described below such that an ultrasound image having the region of interest as a main object is captured. Hereinafter, the ultrasound image captured by this control is referred to as a "region-of-interest image". At this time, the imaging control unit 80 performs control such that the region-of-interest image is captured while directing the ultrasound probe 27 to generate ultrasonic waves toward the region of interest at a plurality of different angles. That is, in this embodiment, the second medical image and the region-of-interest image are captured by the same imaging principle under different imaging conditions. Here, the different imaging conditions mean that the incident angle of ultrasonic waves on the breast and the imaging range are different.

The second medical image according to this embodiment is a group of a plurality of images of the entire region of the breast captured while the ultrasound probe 27 is moved over the entire region of the breast. In contrast, the region-of-interest image according to this embodiment is an ultrasound image having the region of interest as the main object. The region-of-interest image is not a group of a plurality of images of the entire region of the breast, but is a group of a plurality of images obtained by narrowing the imaging position to the position of the region of interest in the entire region of the breast. The group of the plurality of images forming the region-of-interest image includes images captured at the same position at different angles.

In the capture of the first medical image under the control of the imaging control unit 80, the compression control unit 82 performs control to set the compression force of the compression plate 34 against the breast as a first force before the first medical image is captured. Further, in the capture of the second medical image under the control of the imaging control unit 80, the compression control unit 82 performs control to set the compression force of the compression plate 34 against the breast as a second force less than the first force until the second medical image is captured after the first medical image is captured. Furthermore, in the capture of the region-of-interest image under the control of the imaging control unit 80, the compression control unit 82 maintains the compression force of the compression plate 34 against the breast at the second force in a case in which the second medical image is captured.

In addition, the compression control unit 82 sets the second force at which the amount of change in the thickness of the breast in a case in which the compressed state is changed from a state in which the breast is compressed with the first force to a state in which the breast is compressed with the second force is equal to or less than a predetermined amount of change. An example of the predetermined amount of change is the upper limit of the amount of change at which the compression force is changed to the extent that the overlap of the mammary gland tissues, that is, the development of the mammary gland tissues is not changed or the amount of change is within an allowable range even though the overlap is changed.

In a case in which the region of interest has been detected by an analysis unit 92 which will be described below, the compression control unit 82 performs control to release the compressed state of the breast after the region-of-interest image is captured. In addition, in a case in which the region of interest has not been detected by the analysis unit 92 which will be described below, the compression control unit 82 performs control to release the compressed state of the breast without capturing the region-of-interest image.

The image acquisition unit 84 acquires the first medical image, the second medical image, and the region-of-interest image captured under the control of the imaging control unit 80. The image acquisition unit 84 is an example of an acquisition unit according to the technology of the present disclosure. The image output unit 86 outputs the first medical image, the second medical image, and the region-of-interest image acquired by the image acquisition unit 84 to the console 14. The console 14 transmits the first medical image, the second medical image, and the region-of-interest image input from the medical imaging apparatus 12 to the image interpretation support apparatus 16. The position acquisition unit 88 acquires positional information indicating the position of the region of interest transmitted from the console 14 which will be described below or information indicating that the region of interest has not been detected.

Figure 10:
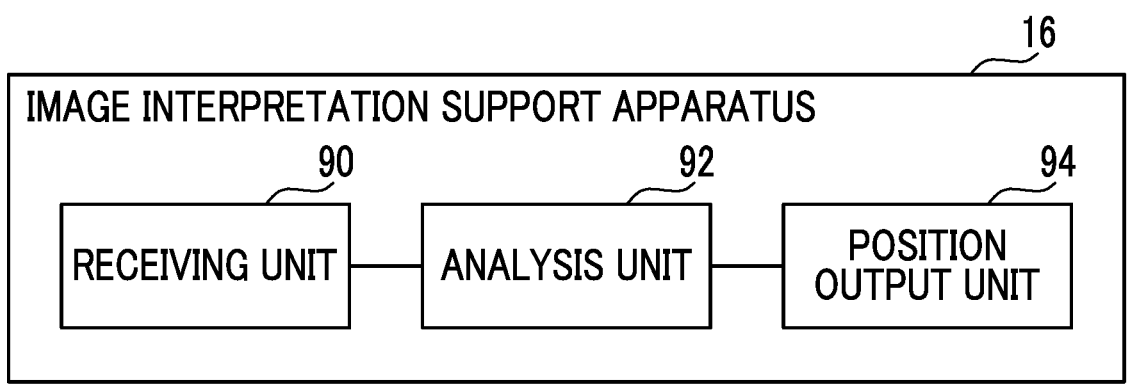
FIG. 10 is a block diagram illustrating an example of the functional configuration of the image interpretation support apparatus.

Next, the functional configuration of the image interpretation support apparatus 16 according to this embodiment will be described with reference to FIG. 10. As illustrated in FIG. 10, the image interpretation support apparatus 16 comprises a receiving unit 90, the analysis unit 92, and a position output unit 94. The CPU 70A executes the analysis processing program 71 to function as the receiving unit 90, the analysis unit 92, and the position output unit 94.

The receiving unit 90 receives the first medical image, the second medical image, and the region-of-interest image transmitted from the console 14. The analysis unit 92 analyzes the first medical image received by the receiving unit 90 using a known technique, such as computer-aided diagnosis (CAD) to detect the region of interest. The region of interest referred to here is a partial region of the first medical image and means a region including a lesion. In addition, the region of interest is not limited to a region that is definitely diagnosed as a lesion and may be a region in which the possibility of a lesion is recognized. In a case in which there are no lesions in the first medical image, the analysis unit 92 does not detect the region of interest. The region of interest is not limited to the region including a lesion and may be, for example, a mammary gland region.

In this embodiment, a period for which the second medical image is captured (hereinafter, referred to as an "imaging period") and a period for which the analysis unit 92 analyzes the first medical image (hereinafter, referred to as an "analysis period") at least partially overlap each other. In addition, how the imaging period and the analysis period overlap each other is not particularly limited as long as the imaging period and the analysis period at least partially overlap each other.

Figure 11A:
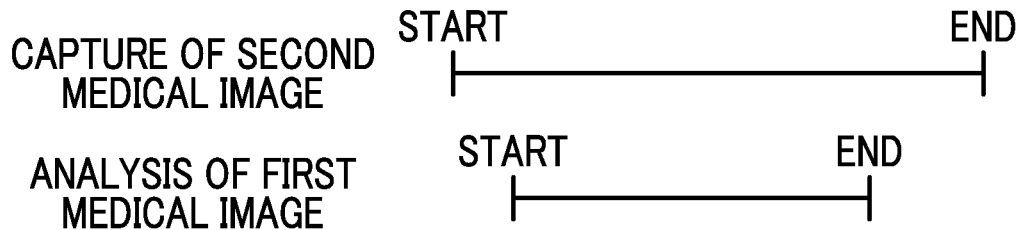
FIG. 11A is a diagram illustrating an example of an overlap state between a period for which a first medical image is analyzed and a period for which a second medical image is captured.
Figure 11B:
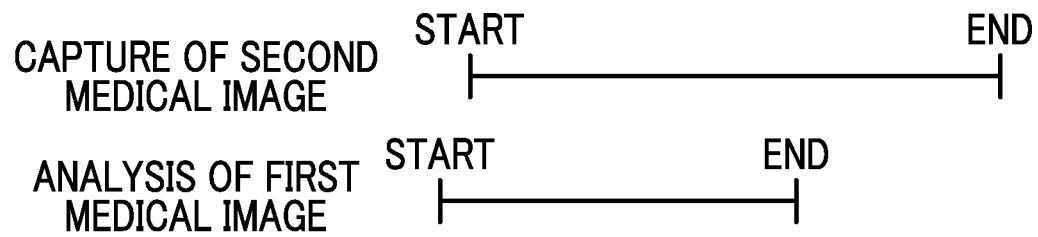
FIG. 11B is a diagram illustrating an example of an overlap state between the period for which the first medical image is analyzed and the period for which the second medical image is captured.
Figure 11C:
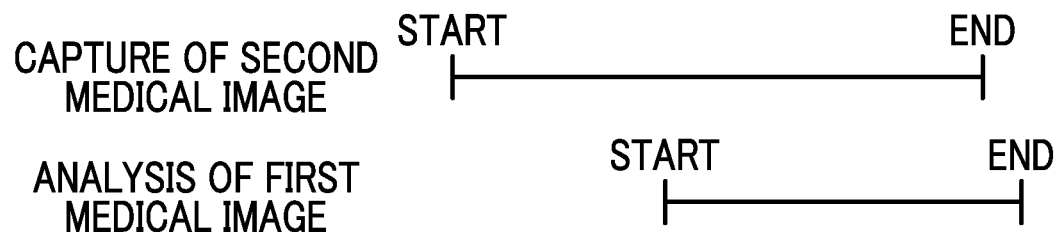
FIG. 11C is a diagram illustrating an example of the overlap state between the period for which the first medical image is analyzed and the period for which the second medical image is captured.
Figure 11D:
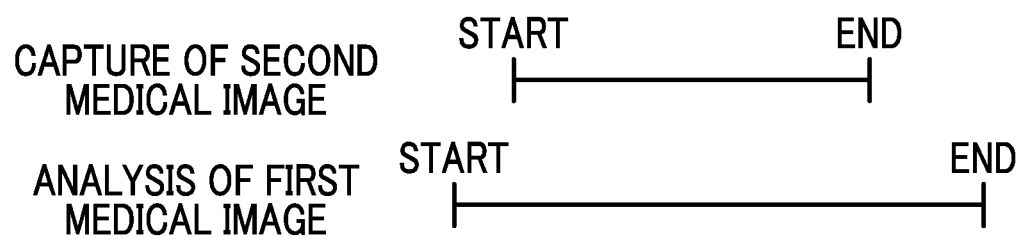
FIG. 11D is a diagram illustrating an example of the overlap state between the period for which the first medical image is analyzed and the period for which the second medical image is captured.

For example, as illustrated in FIG. 11A, the analysis of the first medical image may start after the capture of the second medical image starts and the analysis of the first medical image may end before the capture of the second medical image ends. In addition, for example, as illustrated in FIG. 11B, the analysis of the first medical image may start before the capture of the second medical image starts and the analysis of the first medical image may end before the capture of the second medical image ends. Further, for example, as illustrated in FIG. 11C, the analysis of the first medical image may start after the capture of the second medical image starts and the analysis of the first medical image may end after the capture of the second medical image ends. Furthermore, for example, as illustrated in FIG. 11D, the analysis of the first medical image may start before the capture of the second medical image starts and the analysis of the first medical image may end after the capture of the second medical image ends. Hereinafter, the case illustrated in FIG. 11A will be described as an example.

In a case in which the analysis unit 92 detects the region of interest, the position output unit 94 outputs positional information indicating the position of the region of interest to the console 14. An example of the positional information indicating the position of the region of interest is coordinate information of the region of interest in the first medical image. The console 14 transmits the positional information indicating the position of the region of interest which has been input from the image interpretation support apparatus 16 to the medical imaging apparatus 12. The position output unit 94 is an example of an output unit according to the technology of the present disclosure.

In a case in which the analysis unit 92 has not detected the region of interest, the position output unit 94 outputs information indicating that the region of interest has not been detected (hereinafter, referred to as "non-detection information") to the console 14. The console 14 transmits the non-detection information input from the image interpretation support apparatus 16 to the medical imaging apparatus 12.

Figure 12:
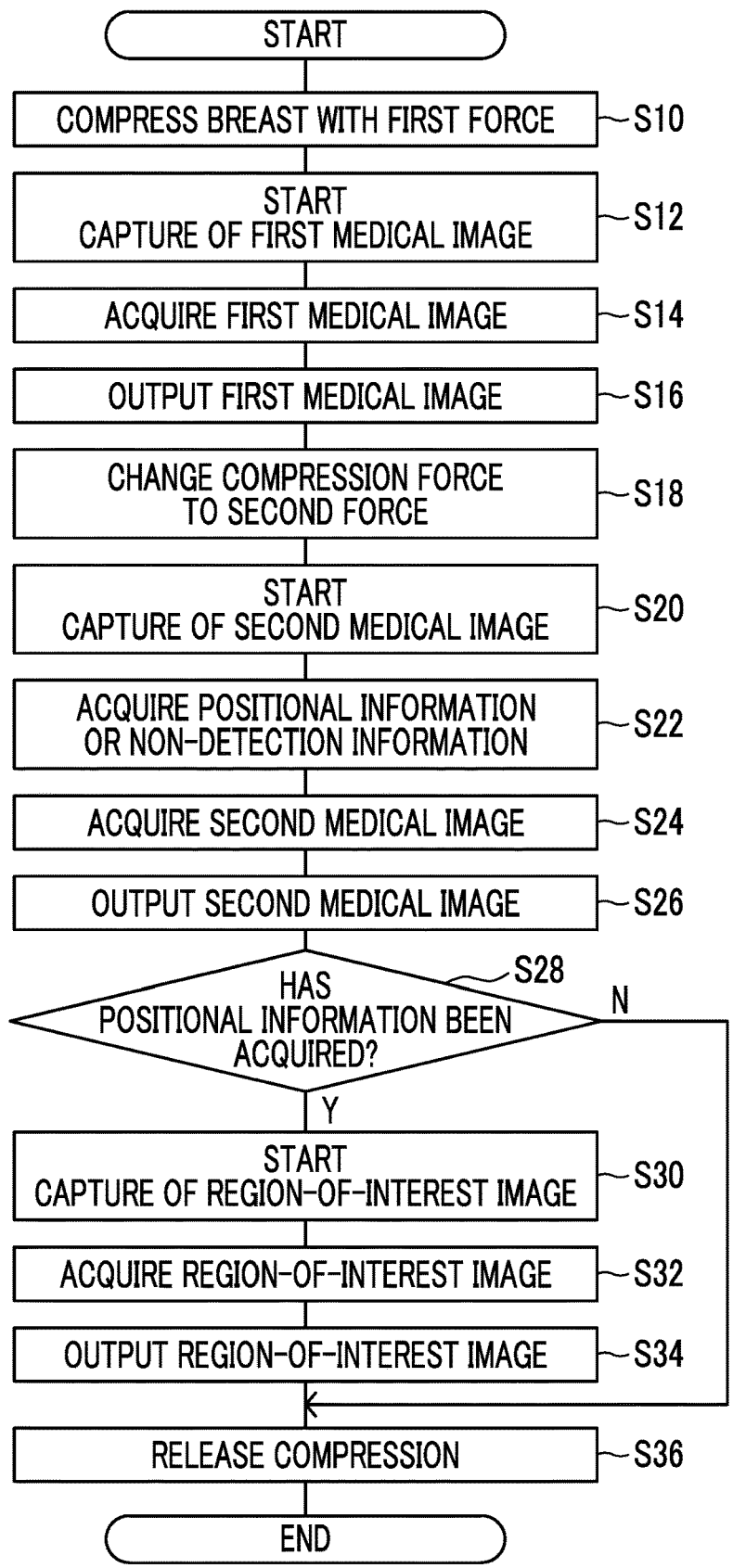
FIG. 12 is a flowchart illustrating an example of an imaging process.

Next, the operation of the medical imaging system 10 according to this embodiment will be described with reference to FIGS. 12 and 13. In a case in which the CPU 20A of the medical imaging apparatus 12 executes the imaging processing program 21, an imaging process illustrated in FIG. 12 is performed. The CPU 70A of the image interpretation support apparatus 16 executes the analysis processing program 71 to perform an analysis process illustrated in FIG. 13. The imaging process illustrated in FIG. 12 and the analysis process illustrated in FIG. 13 may be performed for one or both of the CC imaging or the MLO imaging.

In Step S10 of FIG. 12, the compression control unit 82 performs control to set the compression force of the compression plate 34 against the breast as the first force and to compress the breast with the compression plate 34 as described above. In Step S12, the imaging control unit 80 controls the radiation emitting unit 36 and the radiation detector 30 such that a process of capturing the first medical image of the breast as an object is started. In Step S14, the image acquisition unit 84 acquires the first medical image obtained by completing the imaging started by the process in Step S12.

In Step S16, the image output unit 86 outputs the first medical image acquired by the process in Step S14 to the console 14. The console 14 transmits the first medical image input from the medical imaging apparatus 12 to the image interpretation support apparatus 16 by the process in Step S16. The first medical image transmitted by the console 14 is received by the image interpretation support apparatus 16 in Step S40 which will be described below.

In Step S18, the compression control unit 82 performs control to set the compression force of the compression plate 34 against the breast as the second force less than the first force as described above. In Step S20, the imaging control unit 80 controls the ultrasound probe 27 and the probe moving mechanism 28 such that a process of capturing the second medical image of the breast as an object is started. In Step S22, the position acquisition unit 88 acquires the positional information indicating the position of the region of interest or the non-detection information transmitted from the console 14.

In Step S24, the image acquisition unit 84 acquires the second medical image obtained by completing the imaging started by the process in Step S20. In Step S26, the image output unit 86 outputs the second medical image acquired by the process in Step S24 to the console 14. The console 14 transmits the second medical image input from the medical imaging apparatus 12 by the process in Step S26 to the image interpretation support apparatus 16. The second medical image transmitted by the console 14 is received by the image interpretation support apparatus 16 in Step S48 or Step S54 which will be described below.

In Step S28, the position acquisition unit 88 determines whether or not the information acquired in Step S22 is the positional information indicating the position of the region of interest. In a case in which the information acquired in Step S22 is the non-detection information, the determination result in Step S28 is "No" and the process proceeds to Step S36. In a case in which the determination result in Step S28 is "Yes", the process proceeds to Step S30.

In Step S30, the imaging control unit 80 controls the ultrasound probe 27 and the probe moving mechanism 28 on the basis of the positional information acquired by the process in Step S22 to start the process of capturing the region-of-interest image, as described above. In Step S32, the image acquisition unit 84 acquires the region-of-interest image obtained by completing the imaging started by the process in Step S30.

In Step S34, the image output unit 86 outputs the region-of-interest image acquired by the process in Step S32 to the console 14. The console 14 transmits the region-of-interest image input from the medical imaging apparatus 12 by the process in Step S34 to the image interpretation support apparatus 16. The region-of-interest image transmitted by the console 14 is received by the image interpretation support apparatus 16 in Step S50 which will be described below.

In Step S36, the compression control unit 82 performs control to release the compressed state of the breast. In a case in which the process in Step S36 ends, the imaging process ends.

Figure 13:
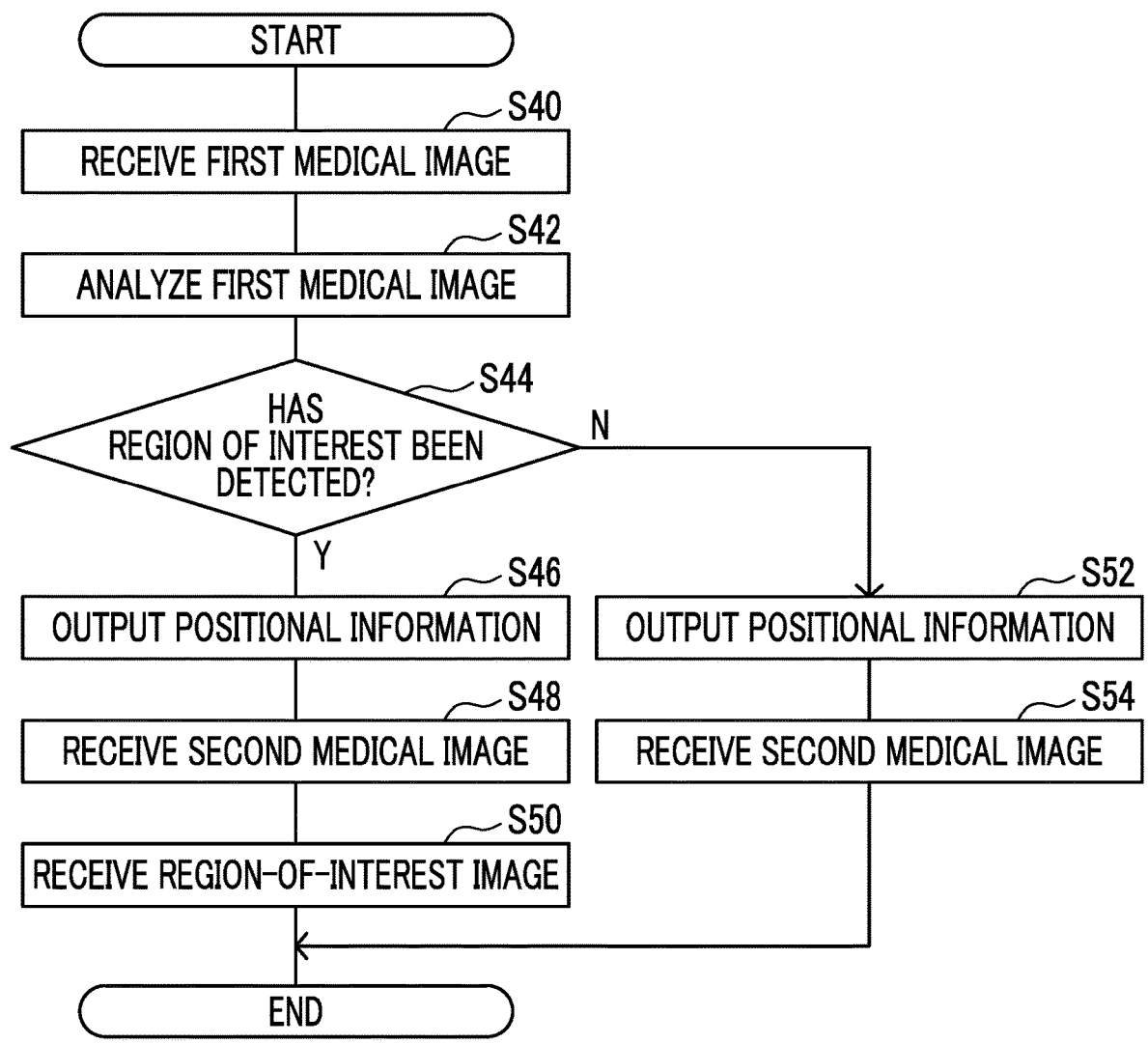
FIG. 13 is a flowchart illustrating an example of an analysis process.

In Step S40 illustrated in FIG. 13, the receiving unit 90 receives the first medical image transmitted from the console 14. In Step S42, the analysis unit 92 performs the process of analyzing the first medical image received by the process in Step S40 to detect the region of interest as described above. In Step S44, the analysis unit 92 determines whether or not the region of interest has been detected in Step S42. In a case in which the determination result is "No", the process proceeds to Step S52. In a case in which the determination result is "Yes", the process proceeds to Step S46.

In Step S46, the position output unit 94 outputs positional information indicating the position of the region of interest detected by the process in Step S42 to the console 14. The console 14 transmits the positional information input from the image interpretation support apparatus 16 by the process in Step S46 to the medical imaging apparatus 12. The positional information transmitted by the console 14 is acquired by the medical imaging apparatus 12 in Step S22.

In Step S48, the receiving unit 90 receives the second medical image transmitted from the console 14. In Step S50, the receiving unit 90 receives the region-of-interest image transmitted from the console 14. In Step S52, the position output unit 94 outputs the positional information indicating the position of the region of interest detected by the process in Step S42 to the console 14 as in Step S46. In Step S54, the receiving unit 90 receives the second medical image transmitted from the console 14 as in Step S48. In a case in which the process in Step S50 ends, the analysis process ends. In a case in which the process in Step S54 ends, the analysis process ends. The first medical image, the second medical image, and the region-of-interest image are used for image interpretation by the user.

As described above, according to this embodiment, for example, as illustrated in FIG. 14, the second medical image is captured after the first medical image is captured. In addition, the region of interest is detected from the first medical image for a period that at least partially overlaps the period for which the second medical image is captured. That is, it is possible to capture the region-of-interest image without waiting for a long time after the second medical image is captured. Therefore, it is possible to shorten the time from the start of the capture of an image of a patient to the interpretation of the image by the user. As a result, it is possible to reduce a burden on the patient.

In the above-described embodiment, the case in which the region-of-interest image is the ultrasound image captured by the same imaging principle as the second medical image has been described. However, the invention is not limited thereto. The region-of-interest image may be a radiographic image captured by the same imaging principle as the first medical image. In this case, the imaging control unit 80 controls the radiation emitting unit 36 and the radiation detector 30 on the basis of the positional information indicating the position of the region of interest acquired by the position acquisition unit 88 such that a radiographic image having the region of interest as the main object is captured after the second medical image is captured. In some cases, this imaging is referred to as spot imaging. At this time, for example, the imaging control unit 80 performs control to capture a region-of-interest image using a larger radiation dose than that in a case in which the first medical image is captured. In this case, the region-of-interest image is a radiographic image having the region of interest as the main object and is an image obtained by narrowing the imaging range to a region having the region of interest as the center in the imaging range of the first medical image.

In the above-described embodiment, the case in which the first medical image is a radiographic image and the second medical image is an ultrasound image has been described. However, the invention is not limited thereto. For example, the first medical image may be an ultrasound image and the second medical image may be a radiographic image.

Further, in the above-described embodiment, the case in which the region-of-interest image is captured using the ultrasound probe 27 provided in the compression unit 46 has been described. However, the invention is not limited thereto. For example, the region-of-interest image may be captured using the hand-held ultrasound probe 27. In this embodiment, the console 14 displays the positional information indicating the position of the region of interest output from the image interpretation support apparatus 16 on the display unit 58. The user takes a region-of-interest image using the hand-held ultrasound probe 27 on the basis of the positional information displayed on the display unit 58.

Further, in the above-described embodiment, the imaging control unit 80 may perform control to capture the region-of-interest image while changing the compressed state of the breast. In this case, for example, the compression control unit 82 controls to increase or decrease the compression force of the compression plate 34 against the breast. In this case, for example, the image interpretation support apparatus 16 derives hardness information of the region of interest on the basis of a difference in the amount of distortion corresponding to a difference in the force of compressing the breast. The user can make a more accurate diagnosis by using the hardness information of the region of interest having a different viewpoint in addition to the radiographic image.

Further, in the above-described embodiment, the case in which the mammography apparatus captures the radiographic image of the breast as an object has been described. However, the invention is not limited thereto. For example, a magnetic resonance imaging (MRI) apparatus may capture the radiographic image of the breast as an object. In this embodiment, for example, the radiographic image and the ultrasound image are captured in a state in which the breast is fixed to the hole of the imaging table.

Further, in the medical imaging apparatus 12 according to the above-described embodiment, the ultrasound probe 27 scans the upper surface of the compression plate 34 to capture an ultrasound image from the side of the radiation source 36R. However, the medical imaging apparatus 12 may be an apparatus that captures an ultrasound image from an opposite side, that is, the side of the imaging table 40.

In addition, each functional unit of the medical imaging apparatus 12 and each functional unit of the image interpretation support apparatus 16 according to the above-described embodiment may be provided in one apparatus. Further, at least one of these functional units may be provided in an apparatus different from the apparatuses of the medical imaging system 10 implemented in the above-described embodiment. In this case, for example, the receiving unit 90, the analysis unit 92, and the position output unit 94 are provided in the console 14.

In addition, in the above-described embodiment, for example, the following various processors can be used as a hardware structure of processing units performing various processes, such as each functional unit of the medical imaging apparatus 12 and each functional unit of the image interpretation support apparatus 16. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In such fashion, various processing units are configured by using one or more of the various processors as the hardware structure.

Furthermore, specifically, an electric circuit (circuitry) obtained by combining circuit elements, such as semiconductor elements, can be used as the hardware structure of the various processors.

In the above-described embodiment, the aspect in which the imaging processing program 21 is stored (installed) in the ROM 20B in advance has been described. However, the invention is not limited thereto. The imaging processing program 21 may be recorded on a recording medium, such as a compact disk read only memory (CD-ROM), a digital versatile disk read only memory (DVD-ROM), or a universal serial bus (USB) memory, and then provided. In addition, the imaging processing program 21 may be downloaded from an external apparatus through the network.

In the above-described embodiment, the analysis processing program 71 is stored (installed) in the ROM 70B in advance. However, the present invention is not limited thereto. The analysis processing program 71 may be provided as recorded on a recording medium, such as a CD-ROM, a DVD-ROM, or a USB memory. The analysis processing program 71 may be downloaded from an external apparatus through the network.

EXPLANATION OF REFERENCES

10: medical imaging system
12: medical imaging apparatus
14: console
16: image interpretation support apparatus
20, 50, 70: control unit
20A, 50A, 70A: CPU
20B, 50B, 70B: ROM
20C, 50C, 70C: RAM
21: imaging processing program
22, 52, 72: storage unit
24, 54, 74: I/F unit
26, 56, 76: operation unit
27: ultrasound probe
28: probe moving mechanism
30: radiation detector
31: motor
32: compression plate driving unit
33: compression force detection sensor
34: compression plate
36: radiation emitting unit
36R: radiation source
37: radiation source driving unit
38: ball screw
39, 59, 79: bus
40: imaging table
40A: imaging surface
42: arm portion
44: base
45: shaft portion
46: compression unit
51: control processing program
58, 78: display
71: analysis processing program
80: imaging control unit
82: compression control unit
84: image acquisition unit
86: image output unit
88: position acquisition unit
90: receiving unit
92: analysis unit
94: position output unit
R: radiation

What is claimed is:
1. A medical imaging system, comprising:
a processor, configured to:
acquire a first medical image obtained by capturing an image of a breast as an object using a first imaging apparatus in a state in which the breast is fixed by compression;
perform control to capture a second medical image of the breast as the object using a second imaging apparatus having a different imaging principle from the first imaging apparatus while the fixation of the breast is maintained, after the first medical image is captured, wherein the second medical image is a group of a plurality of images of an entire region of the breast;
analyze the first medical image to detect a region of interest therefrom for an analysis period, wherein an imaging period for which the second medical image is captured and the analysis period for which the first image is analyzed to detect the region of interest are partially overlap each other; and
output positional information indicating a position of the region of interest so as to capture a region-of-interest image having the region of interest as a main object is captured by the same imaging principle as that of the first imaging apparatus under different imaging conditions from the first medical image or is captured by the same imaging principle as that of the second imaging apparatus under different imaging conditions from the second medical image, after the second medical image is captured by the second imaging apparatus.

2. The medical imaging system according to claim 1, wherein the processor performs control to capture the second medical image in a state in which a force of fixing the breast is different from that in the capture of the first medical image.

3. The medical imaging system according to claim 2, wherein the first medical image is obtained by irradiating the breast with radiation, and
the second medical image is obtained by irradiating the breast with ultrasonic waves.

4. The medical imaging system according to claim 3, wherein the processor performs control to capture the region-of-interest image on the basis of the positional information.

5. The medical imaging system according to claim 4, further comprising:
a plate-shaped compression member that compresses and fixes the breast,
wherein the processor performs control to set a compression force of the plate-shaped compression member against the breast as a first force in the capture of the first medical image and to set the compression force of the plate-shaped compression member against the breast as a second force less than the first force in the capture of the second medical image.

6. The medical imaging system according to claim 5, wherein the processor performs control to capture the region-of-interest image while generating the ultrasonic waves to the region of interest at a plurality of different angles in a state in which the breast is compressed with the same compression force as the compression force against the breast in the capture of the second medical image.

7. The medical imaging system according to claim 5, wherein the processor performs control to capture the region-of-interest image while changing the compressed state of the breast.

8. The medical imaging system according to claim 4, wherein the processor performs control to capture the region-of-interest image while generating the ultrasonic waves to the region of interest at a plurality of different angles in a state in which the breast is compressed with the same compression force as the compression force against the breast in the capture of the second medical image.

9. The medical imaging system according to claim 4, wherein the processor performs control to capture the region-of-interest image while changing the compressed state of the breast.

10. The medical imaging system according to claim 3, further comprising:
a plate-shaped compression member that compresses and fixes the breast,
wherein the processor performs control to set a compression force of the plate-shaped compression member against the breast as a first force in the capture of the first medical image and to set the compression force of the plate-shaped compression member against the breast as a second force less than the first force in the capture of the second medical image.

11. The medical imaging system according to claim 10, wherein the second force is a force at which an amount of change in a thickness of the breast in a case in which the compressed state is changed from a state in which the breast is compressed with the first force to a state in which the breast is compressed with the second force is equal to or less than a predetermined amount of change.

12. The medical imaging system according to claim 11, wherein the processor performs control to capture the region-of-interest image while generating the ultrasonic waves to the region of interest at a plurality of different angles in a state in which the breast is compressed with the same compression force as the compression force against the breast in the capture of the second medical image.

13. The medical imaging system according to claim 10, wherein the processor performs control to capture the region-of-interest image while generating the ultrasonic waves to the region of interest at a plurality of different angles in a state in which the breast is compressed with the same compression force as the compression force against the breast in the capture of the second medical image.

14. The medical imaging system according to claim 10, wherein the processor performs control to capture the region-of-interest image while changing the compressed state of the breast.

15. The medical imaging system according to claim 10, wherein the processor performs control to release the compressed state of the breast in a case in which the processor does not detect the region of interest.

16. The medical imaging system according to claim 1, wherein the analysis period for which the first image is analyzed to detect the region of interest starts after the imaging period for which the second medical image is captured.

17. The medical imaging system according to claim 16, wherein the analysis period for which the first image is analyzed to detect the region of interest starts after and ends before the imaging period for which the second medical image is captured.

18. The medical imaging system according to claim 16, wherein the analysis period for which the first image is analyzed to detect the region of interest starts after and ends after the imaging period for which the second medical image is captured.

19. The medical imaging system according to claim 1, wherein the analysis period for which the first image is analyzed to detect the region of interest starts before and ends after the imaging period for which the second medical image is captured.

20. The medical imaging system according to claim 1, wherein the analysis period for which the first image is analyzed to detect the region of interest starts before and ends during the imaging period for which the second medical image is captured.

* * * * *